US007208309B2

(12) United States Patent
Kukolj et al.

(10) Patent No.: US 7,208,309 B2
(45) Date of Patent: Apr. 24, 2007

(54) INHIBITOR-RESISTANT HCV NS3 PROTEASE

(75) Inventors: George Kukolj, Mont-Royal (CA); Lisette Lagacé, Lorraine (CA); Martin Marquis, Laval (CA); Daniel Lamarre, Terrebonne (CA); Arnim Pause, Montreal (CA)

(73) Assignee: Boehringer Ingelheim International GmbH, Ingelheim (DE)

(*) Notice: Subject to any disclaimer, the term of this patent is extended or adjusted under 35 U.S.C. 154(b) by 439 days.

(21) Appl. No.: 10/695,140

(22) Filed: Oct. 28, 2003

(65) Prior Publication Data

US 2005/0019753 A1 Jan. 27, 2005

Related U.S. Application Data

(60) Provisional application No. 60/421,943, filed on Oct. 29, 2002.

(51) Int. Cl.
*C12N 9/50* (2006.01)
*C12N 15/57* (2006.01)
*C12N 15/70* (2006.01)
*C12N 15/79* (2006.01)

(52) U.S. Cl. ....................... 435/219; 435/23; 435/69.1; 435/252.3; 435/320.1; 435/471

(58) Field of Classification Search ..................... None
See application file for complete search history.

(56) References Cited

U.S. PATENT DOCUMENTS 5,843,752 A * 12/1998 Dasmahapatra et al. .... 435/219
5,990,276 A * 11/1999 Zhang et al. ............... 530/326
6,197,536 B1 3/2001 Steinkuehler et al.
6,326,137 B1 * 12/2001 Hong et al. ..................... 435/5
6,608,027 B1 * 8/2003 Tsantrizos et al. ............. 514/9
6,706,874 B2 * 3/2004 Kukolj et al. ............ 536/23.72
6,986,892 B1 * 1/2006 Coit et al. ............... 424/228.1
2005/0074465 A1 * 4/2005 Houghton ................ 424/189.1

(Continued)

FOREIGN PATENT DOCUMENTS

WO WO 00/59929 10/2000

(Continued)

OTHER PUBLICATIONS

Yamada et al., 1998, "Critical poin mutations for hepatitis C virus NS3 proteinase", Virology, vol. 246, No. 1, pp. 104-112.*

(Continued)

*Primary Examiner*—Nashaat T. Nashed
*Assistant Examiner*—William W. Moore
(74) *Attorney, Agent, or Firm*—Michael Morris; Mary-Ellen M. Devlin; David Dow

(57) ABSTRACT

An inhibitor-resistant HCV NS3 protease is provided which is useful to screen for compounds having therapeutic value against drug resistant HCV strains. In particular, the inhibitor-resistant HCV NS3 protease comprises an amino acid sequence which is mutated in the substrate binding pocket thereof rendering the protease resistant to inhibitor. In a specific aspect of the present invention, at least one of the amino acids at position 155, 156 and 168 of the HCV NS3 protease is mutated to yield an inhibitor-resistant protease.

6 Claims, 3 Drawing Sheets

U.S. PATENT DOCUMENTS

2005/0136400 A1  6/2005  Lin et al.

FOREIGN PATENT DOCUMENTS

WO  WO 02/052015 A2  7/2002
WO  WO 200268933  *  9/2002

OTHER PUBLICATIONS

Llinas-Brunet et al., 1998, "Studies on the C-terminal hexapeptide inhibitors of the hepatitis C virus serine protease", Bioorganic & Medicinal Chemistry Letters, vol. 8, No. 19, pp. 2719-2724.*

Beyer et al., 2001, "Effect of naturally-occurring active site mutations on hepatitis C virus NS3 protease specificity", PROTEINS: Structure, Function, and Genetics, vol. 43, No. 2, pp. 82-88.*

Caterina Trozzi et al; In Vitro Selection and Characterization of Hepatitis C Virus Serine Protease Variants Resistant to an Active-Site Peptide Inhibitor; Journal of Virology Mar. 2003 vol. 7 No. 6 pp. 3669-3679; American Society for Microbiology.

A. Lahm et al; Hepatitis C Virus Proteins as Targets for Drug Development: The Role of Bioinformatics and Modelling; Current Drug Targets (2002) vol. 3 pp. 281-296; Bentham Science Publishers Ltd.

Jan Oliver Koch et al; Determinants of Substrate Specificity in the NS3 Serine Proteinase of the Hepatitis C Virus; Virology (1997) vol. 237 pp. 78-88; Academic Press.

Annarita Casbarra et al; The effect of prome-site occupancy on the hepatitis C virus NS3 protease structure; Protein Science (2002) vol. 11 pp. 2102-2112; Cold Springs Harbor Laboratory Press.

International Serach Report Reference No. PCT/CA 03/01636.

* cited by examiner

INHIBITOR-RESISTANT HCV NS3 PROTEASE

RELATED APPLICATIONS

Benefit of U.S. Provisional Application Ser. No. 60/421,943, filed on Oct. 29, 2002, is hereby claimed, and said application is herein incorporated by reference in its entirety.

FIELD OF THE INVENTION

The present invention relates to a novel HCV NS3 protease, and in particular, to an inhibitor-resistant HCV NS3 protease comprising a mutated amino acid sequence. It also relates to methods of using such an inhibitor-resistant protease to identify inhibitors having activity against HCV strains which have developed resistance to known treatments.

BACKGROUND

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, or so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated: It is not known how HCV interacts with and evades the host immune system. In addition, the roles of cellular and humoral immune responses which protect against HCV infection and disease have yet to be established.

HCV is an enveloped positive strand RNA virus of the Flaviviridae family. The single strand HCV RNA genome is of positive polarity and comprises one open reading frame (ORF) of approximately 9600 nucleotides in length, which encodes a linear polyprotein of approximately 3010 amino acids. In infected cells, this polyprotein is cleaved at multiple sites by cellular and viral proteases to produce structural and non-structural (NS) proteins. The structural proteins (C, E1, E2 and E2-p7) comprise polypeptides that constitute the virus particle. The non-structural proteins (NS2, NS3, NS4A, NS4B, NS5A, NS5B) encode for enzymes or accessory factors that catalyze and regulate the replication of the HCV RNA genome. Processing of the structural proteins is catalyzed by host cell proteases. The generation of the mature non-structural proteins is catalyzed by two virally encoded proteases. The first is the NS2/3 zinc-dependent protease which auto-catalyzes the release of the NS3 protein from the polyprotein. The released NS3 protein contains an N-terminal serine protease domain and catalyzes the remaining cleavages from the polyprotein. The released NS4A protein has at least two roles. The first role is to form a stable complex with NS3 protein and assist in the membrane localization of the NS3/NS4A complex. The second role of the NS4A protein is to act as a cofactor for NS3 protease activity. This membrane-associated complex in turn catalyzes the cleavage of the remaining sites on the polyprotein, thus effecting the release of NS4B, NS5A and NS5B. The C-terminal segment of the NS3 protein also harbors nucleoside triphosphatase and RNA helicase activity. The function of the NS4B protein is unknown. NS5A is a highly phosphorylated protein that appears to be responsible for the interferon resistance of various HCV genotypes. NS5B is an RNA-dependent RNA polymerase (RdRp) that is involved in the replication of HCV.

The open reading frame of the HCV RNA genome is flanked on its 5' end by a non-translated region (NTR) of approximately 340 nucleotides that functions as the internal ribosome entry site (IRES), and on its 3' end by an NTR of approximately 230 nucleotides. Both the 5' and 3' NTRs are important for RNA genome replication. The genomic sequence variance is not evenly distributed over the genome and the 5'NTR and parts of the 3'NTR are the most highly conserved portions.

The cloned and characterized partial and complete sequences of the HCV genome have been analyzed with regard to appropriate targets for prospective antiviral therapies. The following four viral enzyme activities provide possible targets: (1) the NS2/3 protease; (2) the NS3/4A protease complex, (3) the NS3 helicase and (4) the NS5B RNA-dependent RNA polymerase (NS5B RdRp). The NS3 protease has also been crystallized to reveal a structure reminiscent of other serine proteases (Love et al., 1996; Kim et al. 1996).

NS3 protease activity is an attractive target for drug discovery. Enzymatic studies have shown that peptides based on the N-terminal product of the NS5A/5B cleavage site are competitive inhibitors of the enzyme. These peptides have served as a useful starting point in medicinal chemistry efforts to rationally design NS3 protease inhibitors as clinically effective anti-HCV compounds.

Chronic hepatitis C has emerged as an important clinical indication, an effective treatment for which has yet to be developed due to poor response rates to currently existing treatments. For example, the newly approved standard treatment, pegylated-interferon in combination with Ribavirin, exhibits a sustained response rate of 40 to 50%. However, a majority of patients still do not elicit a sustained anti-viral response, particularly against the interferon-resistant HCV genotypes, 1a and 1b.

WO 00/09543, WO 00/09558 and WO 00/59929 (all three incorporated herein by reference) disclose certain types of inhibitors of the HCV NS3 protease that are highly active and selective. These compounds have potential for becoming the next generation of anti-HCV treatment. It can be expected that these inhibitors, as well as many other antiviral treatments, will eventually give rise to viruses that are at least partially resistant to such inhibitors.

Knowledge of mutations which render HCV resistant to inhibitors provides the basis for identifying inhibitors that are effective against such resistant strains. Trozzi et al., 2003 has disclosed a resistant mutant replicon having three individual amino acid substitutions (D168A/Y/V) that render the protease resistant to an inhibitor of the NS3 protease.

Accordingly, in an effort to develop a treatment with long-term efficacy that suppresses or overcomes anti-HCV resistance, we describe a means to identify anti-HCV compounds that exhibit activity against inhibitor resistant HCV strains.

SUMMARY OF THE INVENTION

In a first embodiment, the present invention provides a method for selecting a mutant inhibitor-resistant HCV NS3 protease comprising the steps of:

preparing a nucleic acid construct encoding a selectable marker and native HCV NS3 protease and transfecting host cells with said construct; and incubating the transfected host cells in the presence of an HCV NS3 inhibitor under conditions suitable for selection of transfected cells, wherein colonies resulting from incubation under these conditions render mutant inhibitor-resistant HCV NS3 protease.

According to another aspect of this first embodiment, the present invention provides a method for isolating a mutant inhibitor-resistant HCV NS3 protease wherein the method described above further comprises the steps of:

lysing the cells to release the RNA and using such RNA to produce the resistant-mutant protease; or lysing the cells to release the inhibitor-resistant NS3 protease; and isolating said inhibitor-resistant NS3 protease.

In this regard, the present invention provides in a second embodiment, novel inhibitor-resistant HCV NS3 proteases.

In this regard, the present invention provides in a second embodiment, novel isolated inhibitor-resistant HCV NS3 proteases.

In a third embodiment, the present invention provides recombinant nucleic acids encoding inhibitor-resistant HCV NS3 proteases.

Still, in a third embodiment, the present invention provides isolated recombinant nucleic acids encoding inhibitor-resistant HCV NS3 proteases.

According to another aspect of this third embodiment, there is provided a nucleotide probe capable of hybridizing under stringent conditions to a mutated nucleotide sequence as defined herein for diagnostic purposes.

In a fourth embodiment, vectors incorporating nucleic acids encoding inhibitor-resistant HCV NS3 proteases are provided.

Host cells transfected with these vectors, and cell lines derived therefrom, are provided in a fifth embodiment of the invention.

In a sixth embodiment, the invention encompasses a method for evaluating HCV NS3 protease activity of inhibitor-resistant NS3 proteases in accordance with the invention, comprising the steps of:

incubating host cells transfected with nucleic acid encoding an inhibitor-resistant HCV NS3 protease under conditions which cause the protease to be expressed; and measuring the replication of the nucleic acid in the host cells, wherein the level of replication is proportional to the activity of the expressed protease.

In a seventh embodiment, the invention encompasses a method for identifying potential second generation inhibitors of HCV NS3 protease activity comprising:

incubating host cells transfected with nucleic acid encoding an inhibitor-resistant NS3 protease under conditions which cause expression thereof, in the absence of a candidate second generation inhibitor compound;

incubating host cells transfected with nucleic acid encoding an inhibitor-resistant NS3 protease under conditions which cause expression thereof, in the presence of a candidate second generation inhibitor compound; and measuring the replication of the nucleic acid in the presence and absence of the candidate second generation inhibitor compound, wherein the level of replication of the nucleic acid is proportional to the activity of the expressed protease, and wherein a decrease in activity of the protease in the presence of a candidate second generation inhibitor compound indicates that the compound inhibits the protease.

In an eighth embodiment, the invention encompasses a method for identifying potential second generation inhibitors of HCV NS3 protease activity comprising:

incubating an inhibitor-resistant NS3 protease mutant as defined above in the presence or absence of a candidate second generation inhibitor compound; and measuring the protease activity of the inhibitor-resistant NS3 protease in the presence and absence of the candidate second generation inhibitor compound;

wherein a decrease in activity in the presence of a candidate second generation inhibitor compound indicates that the compound inhibits the inhibitor-resistant NS3 protease.

Other objects, advantages and features of the present invention will become more apparent upon reading the following non-restrictive description of the preferred embodiments with reference to the accompanying drawings in which:

BRIEF DESCRIPTION OF THE DRAWINGS

FIG. 1 illustrates the method by which HCV RNA replication was established in Huh-7 cell culture;

FIG. 2 illustrates neomycin-resistant Huh-7 cell growth in the presence of NS3 protease inhibitor at concentrations ranging from 2 nM to 2000 nM; and FIG. 3 illustrates the clustering of several amino acid substitutions selected with the NS3 protease inhibitors to amino acids that are proximal to the active site (light grey) of the NS3 protease domain. The residues in white indicate the ones identified in resistance studies and located near the bound inhibitor in crystal structure (structure reported in Y. S. Tsantrizos, et al, Angew Chemie v42, 1356).

DETAILED DESCRIPTION OF THE INVENTION

Definitions

Unless defined otherwise, the scientific and technological terms and nomenclature used herein have the same meaning as commonly understood by a person of ordinary skill to which this invention pertains. Generally, the procedures for cell culture, infection, molecular biology methods and the like are common methods used in the art. Such standard techniques can be found in reference manuals such as for example Sambrook et al. (2000) and Ausubel et al. (1994).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (1972).

The present description refers to a number of routinely used recombinant DNA (rDNA) technology terms. Nevertheless, definitions of selected examples of such rDNA terms are provided for clarity and consistency.

The term “recombinant DNA”, “recombinant nucleic acid molecule” or “recombinant plasmid” as known in the art refers to a DNA molecule resulting from the joining of DNA segments. This is often referred to as genetic engineering.

The term “nucleic acid” as it is used with respect to segments, molecules or sequences refers to a unit comprised of nucleotides and, thus, encompasses both DNA molecules and RNA molecules. These segments, molecules or sequences can be isolated from natural sources using techniques established in the art, or can be synthetically derived also using well-established techniques. When read in accordance with the genetic code, these sequences can encode a linear stretch or sequence of amino acids which define a polypeptide, a protein or a protein fragment.

The term "DNA" as it is used with respect to segments, molecules or sequences, is used herein to refer to a chain of nucleotides, each containing the sugar deoxyribose and one of the four bases, adenine (A), guanine (G), thymine (T) or cytosine (C). The term "RNA" refers to a chain of nucleotides, each containing the sugar ribose and one of the four bases adenine (A), guanine (G), uracil (U) or cytosine (C). As one of skill in the art will appreciate, references to DNA which follow are also generally applicable to RNA.

The term "derivative" denotes a modification which comprises the addition of a chemical moiety that imparts on the NS3 mutant protease, or DNA encoding it, one or more desirable properties. Such chemical moieties, for example, can impart improved stability (i.e. biological half life). These moieties can also be used for the purpose of labeling. Moieties capable of providing these and other desirable properties can be found in *Remington's The Science and Practice of Pharmacy* (1995). Methodologies for coupling such moieties to a molecule are well known in the art.

The term "fragment" refers to a segment of an identified inhibitor-resistant mutant NS3 protease-encoding DNA, RNA or amino acid sequence, and/or a segment of any variant or derivative thereof, that substantially retains the capacity to encode an inhibitor-resistant NS3 protease. Such fragments may include, but are not limited to, 5' or 3' truncated nucleotide sequences or terminally truncated amino acid sequences.

The term "expression vector" defines a vector similar to that described above which additionally incorporates the elements necessary to enable the expression of an inserted sequence following transformation or transfection into a host. The cloned gene (inserted sequence) is usually placed under the control of expression control element sequences such as promoter sequences. Such expression control sequences will vary depending on whether the vector is designed to express the inserted sequence in a prokaryotic or eukaryotic host or both (shuttle vectors) and can additionally contain transcriptional elements such as enhancer elements, termination sequences, tissue-specificity elements, and/or translational initiation and termination sites. DNA/RNA is herein referred to as being incorporated "expressibly" into such a vector, and incorporated "expressibly" into a cell, once successful expression from a cell is achieved.

By "eukaryotic expression system" is meant the combination of an appropriate expression vector and a eukaryotic cell line which can be used to express a gene of interest. In all cases, the vector will contain appropriate control elements (promoter) to express the gene in the cell type of interest. Eukaryotic cell types typically used include yeast cells (e.g. *Saccharomyces cerevisiae, Pischia pastoris*) transfected with a plasmid vector; and mammalian cells transfected with DNA vectors for transient or constitutive expression. A preferred cell line useful for the purpose of this invention is derived from liver tissue.

As used herein, the designation "functional derivative" denotes, in the context of a functional derivative of a sequence whether a nucleic acid or amino acid sequence, a molecule that retains a biological activity (either function or structural) that is substantially similar to that of the original sequence. In the present instance, the functional derivative means that the resulting amino acid sequence retains at least a portion of the biological activity of the NS3 protease sufficient to allow the NS3 protease to cleave at least a portion, preferably all its natural substrates i.e. the NS3/4A, 4A/4B, 4B/5A and 5A/5B cleavages sites. In vivo, the NS3 protease activity is retained when the HCV RNA or the virus is able to replicate. This functional derivative or equivalent may be a natural derivative or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid has chemico-physical properties which usually, but not necessarily, are similar to that of the substituted amino acid. The similar chemico-physical properties include, similarities in charge, bulkiness, hydrophobicity, hydrophilicity and the like. Some of the most commonly known conservative amino acid substitutions include, but are not limited to:

Leu or Val or Ile; Gly or Ala; Asp or Glu; Asp or Asn or His; Glu or Gln; Lys or Arg;

Phe or Trp or Tyr; Val or Ala; Cys or Ser; Thr or Ser; and Met or Leu.

The expression "hybridizing under stringent conditions" as used herein means conditions that distinguish at least one or more nucleotide change in the target sequence.

As used herein, the term "inhibitor-resistant" is meant to refer to a mutant HCV NS3 protease that substantially maintains protease activity in the presence of a compound generally known to inhibit native HCV NS3 protease activity. For clarity, "an inhibitor" is a compound that inhibits the cleavage of one or more of the NS3 protease cleavage sites selected from: NS3/4A, NS4A/4B, NS4B/5A, and NS5A/5B. The term "isolated" as used herein means in a state isolated from the cell i.e. any cell-free extract.

For clarity, "mutant HCV NS3 protease" refers to HCV NS3 protease including one or more amino acid mutations, such as amino acid modifications, substitutions, deletions and insertions, that do not result in the elimination of protease activity. As will be understood by one of skill in the art, the activity of a mutant HCV NS3 protease, may vary somewhat from that of native HCV NS3 protease. It will be understood by those of skill in the art, the present invention is meant to encompass inhibitor-resistant mutant NS3 protease and is not, thus, limited to the specific amino acid sequences exemplified herein. The invention also encompasses derivatives or variants of the present mutant NS3 proteases, or fragments thereof, which exhibit resistance to HCV NS3 protease inhibitors. As exemplified herein below, the nucleotide sequences and polypeptides used in the present invention can be modified, for example by in vitro mutagenesis, to dissect the catalytic and structure-function relationship thereof and permit a better design and identification of the resulting proteins.

The term "nucleic acid construct" refers to a strand of nucleic acid composed of nucleic acid sequences which do not normally co-exist. A nucleic acid construct is generally prepared for a specific purpose, and thus, incorporates all the components necessary to achieve that purpose. For example, a nucleic acid construct encoding a specific protein can be prepared which includes the components necessary for the expression of that protein under certain conditions. Vector DNA incorporating exogenous DNA, as discussed below, is an example of a nucleic acid construct.

A host cell or indicator cell has been "transfected" by exogenous or heterologous DNA or RNA (e.g. a DNA construct) when such RNA or DNA has been introduced into the cell. The transfecting RNA or DNA may or may not be integrated (covalently linked) into chromosomal DNA making up the genome of the cell. In prokaryotes, the transfecting/transforming DNA may be maintained on an episomal element such as a plasmid. On the other hand, in eukaryotes, a stably transfected cell is one in which the transfecting DNA becomes integrated with the genomic DNA in chromosomes and is inherited by daughter cells through chromosome replication. Furthermore, in eukaryotes, a stably transfected cell may be one in which the transfecting RNA is maintained as an episomal element such as a replicon. This stability is demonstrated by the ability of the cell to establish cell lines or clones comprised of a population of daughter cells containing the transfecting DNA. Transfection methods are well known in the art as described in Sambrook et al., 1989 and Ausubel et al., 1994.

The term "replicon" as used herein means an RNA molecule that can encode one or more protein molecules and replicates through a complementary RNA strand intermediate.

In order to readily evaluate expression of a gene of interest, a cell can be transfected with a gene that encodes a detectable marker or "reporter" protein along with the gene of interest such that expression of the reporter protein will be indicative of expression of the gene of interest. The term "reporter gene" refers to a nucleotide sequence encoding such a "reporter protein". Examples of commonly used reporter genes include secreted alkaline phosphatase (SEAP), neomycin, luciferase, chloramphenicol amino transferase (CAT), P-galactosidase and green fluorescent protein (GFP).

The term "selectable marker" as used herein means a gene that, when expressed, renders the cell resistant to a selection agent such as an antibiotic (also referred to as selective pressure).

The term "selective pressure" or "selection agent" as used herein interchangeably mean a molecule or compound that, when presented to cells that do not express the selectable marker, will induce cell death. For example, such selection agents can include antibiotics such as: G418, hygromycin, zeomycin or puromycin.

The designation "variant" denotes in the context of this invention an NS3 protease that exhibits inhibitor-resistance as set out above. A variant may be from the same or different species and may be a natural variant or a synthetically derived variant. A variant NS3 protease in accordance with the present invention may incorporate one or more amino acid substitutions, deletions, or additions provided that inhibitor-resistance is conserved. Variations in the nucleotide sequence encoding the present mutant NS3 protease are also encompassed, and these may also include substitutions, deletions, or additions of one or more nucleotides within the sequence provided that the inhibitor-resistance of the protease encoded by the nucleotide sequence is conserved. Variant, derivative and fragment molecules in accordance with the present invention, including both protein and nucleic acid molecules, can be obtained using methods well-known in the art including techniques of isolation/ purification, chemical synthesis and recombinant DNA technology.

The term "vector" refers to a nucleic acid compound used for introducing exogenous nucleic acids into host cells. A vector comprises a nucleotide sequence which can encode one or more protein molecules. Plasmids, cosmids, viruses and bacteriophages, in the natural state or which have undergone recombinant engineering, are examples of commonly used vectors, into which an exogenous genetic sequence or element (either DNA or RNA) may be inserted so as to bring about the replication of the exogenous sequence or element.

Preferred Embodiments

Method of Selecting and Isolating Mutant Inhibitor-Resistant NS3 Protease

In a first embodiment of the present invention, there is provided a method of preparing a mutant inhibitor-resistant HCV NS3 protease.

The method comprises the steps of preparing a nucleic acid construct encoding a selectable marker and native HCV NS3 protease wherein the replication and expression of the selectable marker is dependent on HCV NS3 protease activity. An example is the HCV replicon. Host cells are transfected with this construct and incubated in the presence of an NS3 inhibitor under selective pressure under conditions suitable for selection of successfully transfected cells. Examples of selectable markers are identified above. The appropriate selectable marker will confer on successfully transfected cells a growth advantage under the growth conditions provided to the cells. Colonies resulting from the incubation under these conditions incorporate mutant inhibitor-resistant HCV NS3 protease.

Methods for lysing the cells and isolating the mutant nucleic acid, or ultimately isolating the mutant protease, are well known within the skill of the art, or as described in the following examples.

The nature of the mutations which render the NS3 mutant proteases resistant to the selected inhibitor can readily be identified using standard sequencing techniques which are well-known to those of skill in the art.

Following the first identification of the relevant mutants, validation by further production of similar mutant nucleic acids or proteases can be obtained by site-directed mutagenesis by techniques well-known by the person of skill in the art, or as is described in the following examples.

Mutant Proteases

The present invention provides, in a second embodiment, a novel inhibitor-resistant HCV NS3 mutant protease.

While not bound by any particular theory, in one aspect of this embodiment the mutations to the native NS3 protease, result in a change, perhaps conformational or steric, that prevents, or at least reduces, protease-inhibitor binding such that protease activity is substantially retained. Particularly, mutations in and around amino acids 1–180 of the protease can be mutated such that inhibitor-binding is decreased. More particularly, mutations in and around the active site or close to the inhibitor binding-site can be mutated such that inhibitor-binding is decreased.

In one aspect of this embodiment, the inhibitor-resistant protease is mutated at least one of the amino acid position corresponding to amino acids 155, 156 or 168 of the native HCV NS3 protease sequence. The native amino acid at position 155 is arginine (Arg155 or R155), position 156 is alanine (Ala156 or A156) and position 168 is most often in genotype I an aspartic acid (Asp 168 or D168), though glutamic acid (Glu or E) is also found in some genotype 1 viruses, or glutamine (Gln or Q) is found in genotype 3 viruses. An example of the native amino acid sequence of HCV-1b NS3 protease domain is shown in SEQ ID No: 2.

In accordance with a preferred aspect of the present invention, the inhibitor-resistant NS3 protease has at least one of the amino acid at positions 155, 156 and 168 that is replaced with an amino acid that is not naturally occurring in the HCV NS3 protease at these positions.

The native amino acid at position 155 is arginine (Arg$^{155}$ or R$^{155}$). In accordance with a preferred aspect of the present invention, the inhibitor-resistant NS3 protease in which the arginine at position 155 is replaced with a non-basic amino acid. Replacement of $Arg^{155}$ generally with non basic amino acids such as glutamine (Q) or tryptophan (W) results in an inhibitor-resistant NS3 protease.

In accordance with a preferred aspect of the present invention, the inhibitor-resistant NS3 protease has the alanine at position 156 that is replaced with any other amino acid. In another aspect of this embodiment, the inhibitor-resistant protease is mutated at Ala 156 generally with uncharged amino acids such as glycine (G), threonine (T) or valine (V), resulting in an inhibitor-resistant NS3 protease. Alternatively, the inhibitor-resistant protease is mutated at Ala 156 generally with uncharged amino acids having a slightly larger side chain such as threonine (T) or valine (V), resulting in an inhibitor-resistant NS3 protease.

In another aspect of this embodiment, the inhibitor-resistant protease is mutated at amino acid position 168. The native amino acid at position 168 is aspartic acid ($Asp^{168}$ or $D^{168}$) glutamic acid (Glu or E) or glutamine (Gln or Q). In accordance with a preferred aspect of the present invention, the inhibitor-resistant NS3 protease has the aspartic acid/glutamic acid/glutamine at position 168 that is replaced with any other amino acid. Replacement of $Asp^{168}$ generally with amino acids such as glycine (G), alanine (A), asparagine (N), histidine (H) or valine (V) results in an inhibitor-resistant NS3 protease. Preferably, the inhibitor-resistant NS3 protease has the aspartic acid/glutamic acid/glutamine at position 168 that is replaced with an uncharged amino acids with small side chains such as glycine (G), alanine (A), asparagine (N) or valine (V) results in an inhibitor-resistant NS3 protease. More preferably, the Asp/Glu/Gln168 is mutated to alanine (A) or valine (V). Alternatively, in a further preferred embodiment, the native Asp/Glu/$Gln^{168}$ of the NS3 protease is replaced with glycine (G), asparagine (N) or histidine (H).

In a further preferred aspect of this embodiment, the native $Arg^{155}$ of the NS3 protease is replaced with glutamic acid.

In a preferred aspect of this embodiment, the native $Ala^{156}$ of the NS3 protease is replaced with valine.

In a further preferred aspect of this embodiment, the native $Asp^{168}$ of the NS3 protease is replaced with valine.

In a preferred aspect of this embodiment, at least one of native $Ala^{156}$ and $Asp^{168}$ of the NS3 protease is replaced with valine.

In a further preferred aspect of this embodiment, both of native $Ala^{156}$ and $Asp^{168}$ of the NS3 protease are replaced with valine.

Another aspect of the present invention covers a NS3 protease domain comprising a sequence having 90% identity to the sequence shown in SEQ ID No.2 wherein the amino acid sequence is mutated as defined above.

Alternatively, in a further preferred aspect of this embodiment, any one of the mutations presented in Tables 1, 2, 3 or 4 can lead to an inhibitor-resistant mutant HCV NS3 protease.

Recombinant Nucleic Acid Molecules

In a third embodiment, the invention encompasses recombinant nucleic acid molecules, including both DNA and RNA molecules that encode mutant HCV inhibitor-resistant NS3 proteases as defined above. An example of the nucleotide sequence encoding a native HCV NS3 protease domain is set out in SEQ ID No: 1. Modifications in this sequence which encode mutant inhibitor-resistant NS3 proteases as determined using methods known to those of skill in the art, such as the cell-based assays described in the specific examples herein, are encompassed, including variants, derivatives and fragments thereof. These sequence modifications may also, of course, incorporate modifications that result from the degeneracy of the nucleic acid code.

In one aspect of the present invention, the nucleic acid molecule encodes a mutant HCV inhibitor-resistant NS3 protease which is modified at at least one of the amino acid as defined above.

Nucleic Acid Constructs, Vectors, Replicon and Viruses

In a fourth embodiment, the invention encompasses nucleic acid constructs, vectors, replicons and viruses comprising a nucleic acid molecule encoding a mutant HCV inhibitor-resistant NS3 protease as described above.

In one aspect of this embodiment, nucleic acid constructs encoding inhibitor-resistant NS3 protease are prepared in which nucleic acid encoding the mutant protease is linked to nucleic acid encoding a selectable marker.

In a particular aspect of this embodiment, the mutant HCV inhibitor-resistant NS3 protease-encoding nucleic acid is incorporated "expressibly" into a construct or vector. In order to achieve expression, the protease-encoding nucleic acid is linked to elements within the construct or vector which are appropriate to allow for expression of the protease-encoding nucleic acid on transfection, stably or transiently, into a host cell. Expression constructs and vectors are well-known to those of skill in the art as described above.

Transfected Host Cells

In a fifth embodiment, host cells transfected with an expression vector or a replicon comprising a nucleic acid molecule encoding a mutant HCV inhibitor-resistant NS3 protease are provided, as well as cell lines derived from such host cells.

In one aspect of the preferred embodiment, there is provided appropriate expression systems and prokaryotic or eukaryotic cells for expression of the mutant HCV NS3 protease.

Preferred aspects of this embodiment, provide expression systems in *E. coli*, baculovirus, yeast as well as mammalian cells such as in Huh-7 cells.

In a preferred aspect of this embodiment, there is provided a mammalian host cell transfected with a vector or a replicon, or infected with a virus, comprising a nucleic acid molecule encoding a mutant inhibitor-resistant NS3 protease, either stably or transiently. Non-limiting examples of appropriate mammalian host cells and cell lines include primary hepatocytes, liver cell lines, fibroblasts, lymphocytes, and kidney cell lines.

In a further preferred aspect, a human host cell line is provided that is transfected with a mutant inhibitor-resistant NS3 protease-encoding nucleic acid. In a more preferred aspect, the transfected human host cell line is selected from a liver or kidney cell line. Examples of preferred host cells include human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11), Huh-7 cells, WRL68 cells, HepG2 cells and Chang cells.

Method for Evaluating Protease Activity

In a sixth embodiment of the present invention, there is provided a method of evaluating NS3 protease activity of a mutant HCV NS3 protease in accordance with the present invention.

The method comprises the steps of incubating host cells transfected with nucleic acid encoding an inhibitor-resistant NS3 protease under conditions which cause the protease to be expressed; and measuring the replication of the nucleic acid, wherein the level of replication is proportional to the activity of the expressed protease. As one of skill in the art will appreciate, the level of replication as well as the protease activity can be measured (directly or indirectly) using standard assays established for this purpose, such as the assays described in detail in the specific examples that follow.

Methods for evaluating protease activity include but are not limited to, replicon assays, surrogate cell based assays, or purified NS3 protease in vitro enzymatic assays.

Method for Identifying Inhibitors

In a seventh embodiment of the present invention, there is provided a method of screening candidate second generation inhibitor compounds for the ability to inhibit the activity of mutant HCV NS3 protease in accordance with the present invention. In an eighth embodiment of the present invention, there is provided a method of screening candidate second generation inhibitor compounds for the ability to inhibit the activity of mutant HCV NS3 protease in cell-free assay in accordance with the present invention.

In one aspect, the method of identifying potential second generation inhibitor compounds of HCV NS3 protease comprises incubating an isolated inhibitor-resistant NS3 protease mutant as defined above in the presence or absence of a candidate second generation inhibitor compound; and measuring the protease activity of the inhibitor-resistant NS3 protease in the presence and absence of the candidate second generation inhibitor compound. A decrease in activity in the presence of a candidate second generation inhibitor compound indicates that the compound inhibits the inhibitor-resistant NS3 protease.

In another aspect, the method of identifying potential second generation inhibitor compounds of an HCV NS3 protease comprises incubating host cells transfected with nucleic acid encoding an inhibitor-resistant NS3 protease in the presence of a candidate second generation inhibitor compound under conditions which cause expression thereof; incubating host cells transfected with nucleic acid encoding an inhibitor-resistant NS3 protease in the absence of a candidate second generation inhibitor compound under conditions which cause expression thereof; and then measuring the replication of the nucleic acid, wherein the level of replication of the nucleic acid is proportional to the protease activity in each case. A decrease in protease activity in the presence of a candidate second generation inhibitor compound indicates that the candidate compound inhibits the protease.

The cell-based assays and methods of the present invention are conducted under conditions for mammalian cell growth that are well known to a person skilled in the art, i.e. physiological pH, salt concentrations using buffers such as PBS, temperatures between 30° and 42°, appropriate cell culture media and providing sufficient time for cell growth. More specifically, the transfected host cells are incubated for a sufficient time to allow for expression of the mutant NS3 inhibitor-resistant protease, for example, an incubation period of at least 1 hour, but more preferably, an incubation period of from 10 hours to about 24 hours.

The assays and methods of the present invention are conducted under conditions for measuring NS3 protease activity that are well known to a person skilled in the art, i.e. physiological pH, salt concentrations using buffers such as Tris, HEPES, temperatures between 15° and 37° (preferably at room temperature), appropriate incubation and detection techniques.

Preferred aspects of embodiments of the present invention are described in the following specific examples which are not to be construed as limiting.

EXAMPLES

Example 1

Identification of HCV NS3 Mutants Resistant to a Macrocyclic Peptide HCV Inhibitor The method described by Lohmann et al. (1999, Science 285:110) was used to mimic the replication of subgenomic HCV RNA in a system that is dependent on the function of HCV non-structural proteins and enzymes. This HCV RNA replicon system incorporates two cistrons: one encoding the HCV non-structural region and the second encoding a selectable neomycin resistant marker (i.e. gene encoding neomycin phosphotransferase). As one of skill in the art will appreciate, the second cistron may encode any marker suitable for selection purposes. Cell lines harboring such bicistronic, subgenomic HCV RNA, such as the S22.3 cell line, are described by Kukolj and Pause (see WO 02/052015, the contents of which are hereby incorporated by reference). These cell lines are useful in evaluating the efficacy and potency of potential anti-HCV therapeutics that inhibit one or more of the HCV non-structural proteins.

Figure 1:
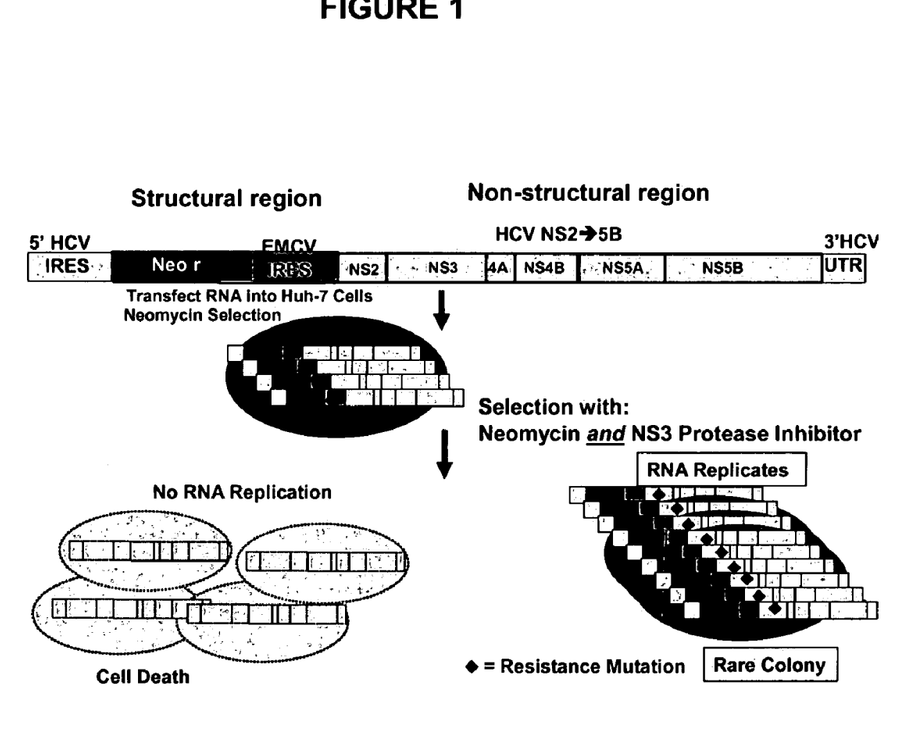
Figure 2:
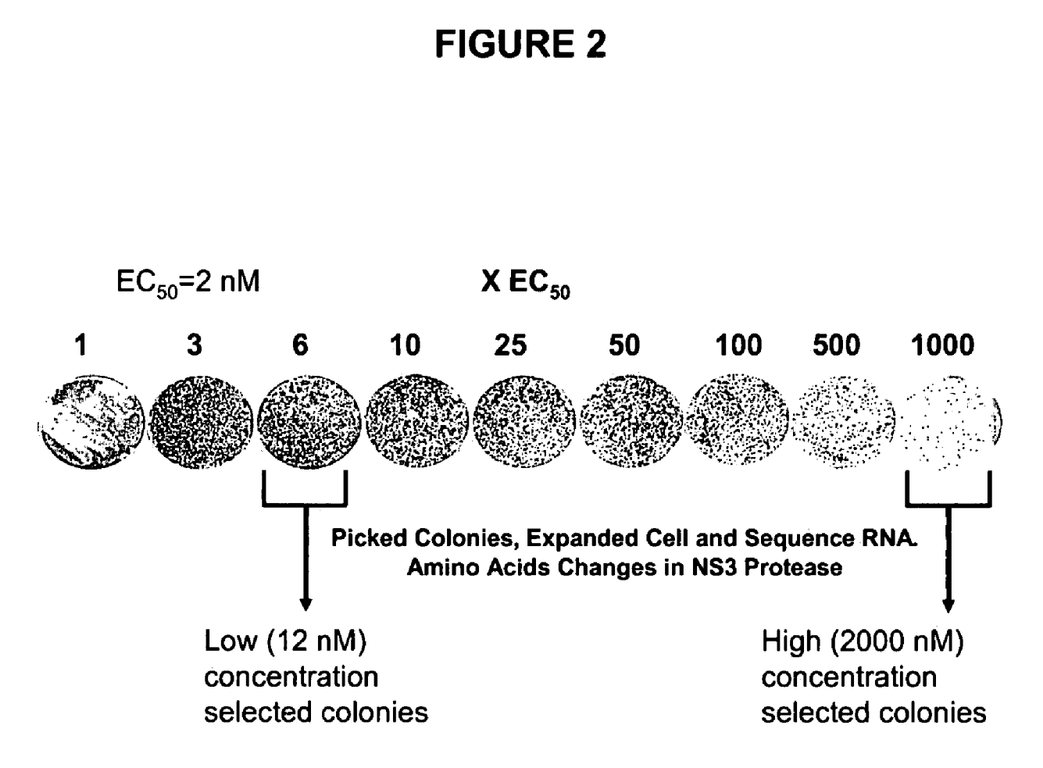

The present method by which HCV RNA replication was established in cell culture is summarized in FIG. 1. As shown, Huh-7 cells ($8 \times 10^6$ cells) were transfected with the bicistronic subgenomic HCV RNA using transfection methods well-established in the art. Transfected Huh-7 cells were selected by growth in neomycin-containing media (0.5 mg/ml neomycin). Specifically, transfected cells replicate the RNA that produces neomycin phosphotransferase thereby rendering the cells resistant to the cytotoxic effect of neomycin. Mutated HCV replicons as described in WO 02/052015 can also be used in accordance with the present method to increase RNA replication and efficiency of replicon establishment.

In short, the selection of S22.3 cell lines resistant to NS3 protease inhibitors was as follows: S22.3 cells were trypsinized and resuspended in fresh media (DMEM, 10% fetal calf serum) with 1 mg/ml G418 antibiotic. 150,000 cells were plated into one well of a 6-well plate. The following day (t=day 0), fresh medium containing the NS3 protease inhibitor at a pre-determined concentration and 1 mg/ml G418 was added to the well. After cells reached confluency on day 3, the S22.3 cells were trypsinized and passed into a 10 cm plate. Medium (containing inhibitor and 1 mg/ml G418) was changed on day 6 and day 10. By day 11, cell death was evident as, the majority of cells had lost resistance to G418. At day 14 fresh medium was changed which now contained a pre-determined concentration of NS3 protease inhibitor with 0.5 mg/ml G418. Medium with inhibitor and 0.5 mg/ml G418 was replenished at day 17 and day 20. The cells that formed colonies by day 21 were picked for expansion into 48-well plates, and the colonies were counted by fixing and staining the cells with crystal violet. Resistant cell lines were propagated from 48-well to 24-well to 6-well and beyond. The total cellular RNA that also contained the HCV subgenomic replicon RNA was isolated from 1,000,000 cells (or more) by Qiagen RNeasy® cartridge and protocol. HCV sequence was amplified by RT-PCR and the NS3 region was sequenced with NS3 specific primers.

Specifically, neomycin-resistant cell colonies were then exposed to a known NS3 protease inhibitor, specifically, a macrocyclic peptide inhibitor:

inhibitor A=cyclopropa[e]pyrrolo [1,2-a][1,4]diazacyclopentadecine-14a(5H)-carboxylic acid, 6-[[(cyclopentyloxy)carbonyl]amino]-1,2,3,6,7,8,9,10,11,13a, 14,15,16,16a-tetradecahydro-2-[[7-methoxy-2-[2-[(1-methylethyl)amino]-4-thiazolyl]-4-quinolinyl]oxy]-5,16-dioxo-, (2R,6S, 12Z, 13aS, 14aR, 16aS), which is described as compound #822 in WO 00/59929, the contents of which is hereby incorporated by reference. The colonies were grown in the presence of increasing concentrations of this inhibitor ($EC_{50}$ of 2 nM) ranging from 2 nM to 2000 nM.

Colonies emerging in the presence of low ($6 \times EC_{50}$ or 12 nM) and high ($1000 \times EC_{50}$ or 2000 nM) concentrations of inhibitor A were expanded and the replicon was RNA sequenced over the NS3/4A region using standard sequencing techniques. Mutations detected in the NS3 protease domain at both high and low inhibitor concentrations are summarized below in Table 1.

Amino acids are referred by 1-letter code, the native HCV NS3 protease amino acid preceding its position number in the protease and the mutant amino acid following the position number, e.g. D168G indicates the native aspartic acid at position 168 is replaced by glycine in the mutant protease.

TABLE 1

| Low Inhibitor [ ] (12 nM) | | High Inhibitor [ ] (2000 nM) | |
| --- | --- | --- | --- |
| nucl change | AA change | nucl change | AA change |
| A503G | D168G | G466A– A503G | A156T D168A |
| A211G–G466A | I71V A156T | C467T | A156V |
| A257G–A503G | Q86R D168G | C467T | A156V |
| A503G | D168G | C467T | A156V |
| C467T | A156V | C467T | A156V |
| A503G | D168G | C265T– C467T | P89S A156V |
| G464A | R155Q | C265T– C467T | P89S A156V |
| A503T | D168V | A503T | D168V |
| A122G | Q41R | C467T | A156V |
| C467T | A156V | C266T– C467T | P89L A156V |
| A503G | D168G | C467T | A156V |
| G502R | D168N/D | C467T | A156V |
| G502A–A532T | D168N T178S | A503T | D168V |
| A239G–G331T | Q80R A111S | A503T | D168V |
| G502C | D168H | A503T | D168V |
| C467T | A156V | C467T | A156V |
| C467T | A156V | G466A | A156T |
| A257G–A503G | Q86R D168G | C467T | A156V |
| C315T | D168E | C467T | A156V |
| C467T | A156V | C467T | A156V |
| G526A | E176K | | |

Figure 3:
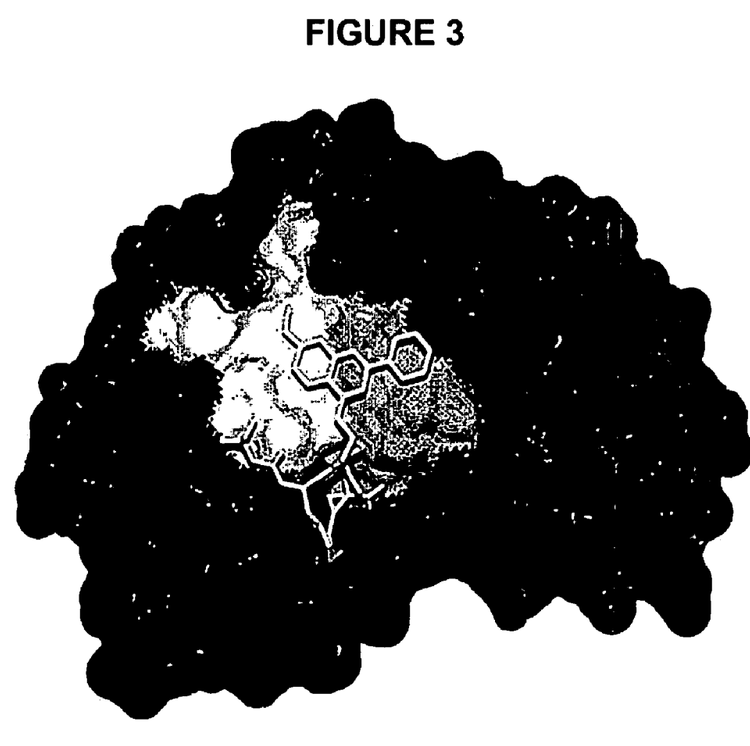

The results show that a variety of amino acid mutations occurred in the proximity of the active site (see black amino acids in FIG. 3), particularly in colonies isolated at low inhibitor concentration. The mutations, alanine to valine or threonine at position 156 (A156V/Y) and aspartic acid to valine/alanine at position 168 (D168V/A) were consistently observed in colonies isolated at high inhibitor concentration. In particular, the mutation, A156V, was detected in 70% of the sequenced colonies grown at high inhibitor concentration, while the mutation, D168V, was detected in 20% of the sequenced colonies grown at high inhibitor concentration.

Example 2

Identification of HCV NS3 Mutants Resistant to NS3 Inhibitor B

The method described above in Example 1 was used to identify NS3 protease mutants that occurred by growth in the presence of NS3 protease inhibitor:

inhibitor B=cyclopropane carboxylic acid, N-[(cyclopentyloxy)carbonyl]-3-methyl-L-valyl-(4R)-4-[[2-[2-(acetylamino)-4-thiazolyl]-7-methoxy-4-quinolinyl]oxy]-L-prolyl-1-amino-2-ethenyl-, (1R,2S)-, which has an $EC_{50}$ of 40 nM.

Colonies emerging in the presence of low ($3 \times EC_{50}$ or 120 nM) and high ($50 \times EC_{50}$ or 2000 nM) concentrations of inhibitor were expanded and the replicon RNA was sequenced over the NS3/4A region using standard sequencing techniques. Mutations detected in the NS3 protease domain at both high and low inhibitor concentrations are summarized below in Table 2.

TABLE 2

| Low Inhibitor [ ] (120 nM) | | High Inhibitor [ ] (2000 nM) | |
| --- | --- | --- | --- |
| nucl change | AA change | nucl change | AA change |
| C467G | A156G | C467T | A156V |
| G115A–C430T– A503T | A39T L144F D168V | C467T | A156V |
| A503G | D168G | C467T | A156V |
| C266T–G464A | P89L R155Q | C467T | A156V |
| C467T | A156V | A503T | D168V |
| G77A–A503G– A535G | R26K D168G M179V | | |
| C467T–G537A | A156V M179I | | |
| A122G–A503G | Q41R D168G | | |
| C366A | S122R | | |
| C265T–C366A | P89S S122R | | |
| A211G–G502A | I71V D168N | | |
| G502A | D168N | | |
| A503C | D168A | | |
| C266T–G464A | P89L R155Q | | |

Again, the results show that a variety of amino acid mutations occurred in the proximity of the inhibitor binding pocket, particularly in colonies isolated at low inhibitor concentration, and the individual mutations, A156V/G, and D168V/N/A/G were consistently observed in colonies isolated at low and high inhibitor concentration. The mutation, A156V, was detected in 80% of the sequenced colonies grown at high inhibitor concentration, while the mutation D168V was detected in 20% of the sequenced colonies grown at high inhibitor concentration.

Example 3

Identification of HCV NS3 Mutants Resistant to Another NS3 Inhibitor

The method described above in Example 1 was used in conjunction with NS3 protease inhibitor:

inhibitor C=Cyclopropa[e]pyrrolo[1,2-a][1,4]-diazacyclopentadecine-14a(5H)-carboxylic acid, 2-[[2-[2-(acetylamino)-4-thiazolyl]-7-methoxy-4-quinolinyl]oxy]-6-[[(1,1-dimethylethoxy)carbonyl]amino]-1,2,3,6,7,8,9,10,11,13a,14,15,16,16a-tetradecahydro-5,16-dioxo-, (2R,6S, 12Z, 13aS, 14aR, 16aS)-, which is also described as compound #702 in WO 00/59929 (incorporated herein by reference) which has an $EC_{50}$ of 5 nM.

Colonies emerging in the presence of low (6×$EC_{50}$ or 30 nM), intermediate (20×$EC_{50}$, 100 nM) and high (100×$EC_{50}$, 500 nM and 200×$EC_{50}$, 1000 nM) concentrations of inhibitor were expanded and the replicon RNA was sequenced over the NS3/4A region using standard sequencing techniques. Mutations detected in the NS3 protease domain at different concentrations are summarized below in Table 3.

TABLE 4

| Inhibitor [7.5 nM] | | Inhibitor [700 nM] | |
| --- | --- | --- | --- |
| nucl. change | AA change | nucl. change | AA change |
| A503G | D168G | A503T | D168V |
| A503T | D168V | G466A | A156T |
| A503C | D168A | A503C/T | D168A, V |
| G464A | R155Q | | |
| G502A, G464A | D168N, R155Q | | |
| C467T | A156V | | |

The results show that a selected number of amino acid mutations occurred in the proximity of the active site. The

TABLE 3

| Low Inhibitor [ ] (30 nM) | | Intermediate [ ] (100 nM) | | High Inhibitor [ ] (500 nM) | | High Inhibitor [ ] (1000 nM) | |
| --- | --- | --- | --- | --- | --- | --- | --- |
| nucl change | AA change | nucl change | AA change | AA change | AA change | nucl change | AA change |
| G466A | A156T | G466A | A156T | A84G A504T | Q28R D168V | A503T/C | D168V |
| C449T C467T | A150V A156V | A504C | D168A | A84G A504T | Q28R D168V | A503T | D168V |
| G59A C343T C430T A503G | S20N P115S L144F D168G | A504T | D168V | C467T | A156V | G466A | A156T |
| G466A A239G | A156T Q80R | G466A G466A G472C | A156T A156T V158L | A504T A504T T536C | D168V D168V M179Y | C467T A503T | A156V D168V |
| G466A C463T | A156T R155W | | | | | C467T G302A A503C | A156V S101N D168A |
| A239G A503T C467T | Q80R D168V A156V | | | | | | |

The results show that a variety of amino acid mutations occurred in the proximity of the active site, and the mutations A156V/T, and D168V/A/G were consistently observed.

Example 4

Identification of HCV NS3 Mutants Resistant to a Macrocyclic Peptide HCV Inhibitor in Another Cell Line Harboring a Bicistronic Subgenomic HCV RNA Cell line R3 was derived from S22.3 and contains bicistronic HCV replicon with mutations that confer adaptivity to replicate in Huh7 cells (WO 02/052015 incorporated herein by reference). Inhibitor A described above in Example 1 was used to identify NS3 protease mutants in R3 cell lines.

Colonies emerging in the presence of 7.5 nM and 700 nM of inhibitor A were expanded and the replicon RNA was sequenced over the NS3/4A region using standard sequencing techniques. Mutations detected in the NS3 protease domain at both concentrations are summarized in Table 4.

individual mutations, aspartic acid to either valine (D168V), or alanine (D168A) or glycine (D168G) were observed more frequently at the low concentration of inhibitor while D 168V was more frequently observed at high concentration of inhibitor.

Example 5

Determination of Inhibitor $EC_{50}$ Using NS3 Mutant Replicon Cell Lines

Specific isogenic HCV subgenomic replicon cDNAs individually containing only one of the inhibitor-resistant mutations, i.e. (in this example: A156T; or A156V; or D168V; or D168G) were cloned and corresponding in vitro transcribed RNA of these modified bi-cistronic replicons were generated. The mutant-encoding RNAs were used to construct mutant-containing replicon cell lines in naïve Huh-7 cells as described previously for other HCV replicons. Each of these individual replicon cell lines were then used to confirm the decrease in inhibition exhibited by NS3 protease inhibitor A on the NS3 mutants. They were also used to determine the level of inhibition of the mutant inhibitor-resistant cell lines in the presence of an unrelated HCV NS5B polymerase inhibitor or alpha-interferon. Using the assay described in WO 03/010141 (Example 48) the $EC_{50}$ of each inhibitor was determined using the mutant cell lines. The results of these experiments are summarized below in Table 5.

TABLE 5

| Inhibitor | WT | A156T | A156V | D168V | D168G |
|---|---|---|---|---|---|
| A | 0.0009 | 0.547 | 0.324 | 0.735 | 0.023 |
| polymerase inhibitor | 1.39 | 1.34 | 1.19 | 1.38 | 1.13 |
| IFN-α | 0.23 | 0.21 | 0.23 | 0.20 | 0.18 |

Note that each of these four mutants only shift the potency of the related NS3 protease inhibitors and have no effect on the $EC_{50}$ of an unrelated HCV NS5B polymerase inhibitor or interferon-alpha. The D168V and A156T mutants are most detrimental to this class of NS3 protease inhibitors, shifting the cell culture $ Compound F has the following structure:

TABLE 7

(F)

[Chemical structure diagram of Compound F]

| Inhibitor | K$_i$ (nM) | | | |
|---|---|---|---|---|
| | WT | A156T | D168V | R155Q |
| A | 5.6 | 800* | 970* | 220* |

*calculated K$_i$ from IC$_{50}$

CONCLUSION

A method for the selection of HCV sub-genomic RNAs that replicate in the presence of various inhibitors of HCV NS3 protease is

```
<400> SEQUENCE: 2

Ala Pro Ile Thr Ala Tyr Ser Gln Gln Thr Arg Gly Leu Leu Gly Cys
1               5                   10                  15

Ile Ile Thr Ser Leu Thr Gly Arg Asp Arg Asn Gln Val Glu Gly Glu
            20                  25                  30

Val Gln Val Val Ser Thr Ala Thr Gln Ser Phe Leu Ala Thr Cys Val
        35                  40                  45

Asn Gly Val Cys Trp Thr Val Tyr His Gly Ala Gly Ser Lys Thr Leu
    50                  55                  60

Ala Gly Pro Lys Gly Pro Ile Thr Gln Met Tyr Thr Asn Val Asp Gln
65                  70                  75                  80

Asp Leu Val Gly Trp Gln Ala Pro Pro Gly Ala Arg Ser Leu Thr Pro
            85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
            115                 120                 125

Pro Arg Pro Val Ser Tyr Leu Lys Gly Ser Ser Gly Gly Pro Leu Leu
            130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Val Pro Val Glu Ser Met Glu
                165                 170                 175

Thr Thr Met Arg
            180
```

What is claimed is:

1. An isolated, variant, inhibitor-resistant, HCV NS3 protease having serine protease activity comprising an HCV NS3 protease amino acid sequence wherein said variant comprises a substitution of the amino acid at the position corresponding to position 156 of SEQ ID NO:2 with a non-alanine amino acid.

2. The variant protease according to claim 1, wherein said amino acid sequence set forth in SEQ ID NO:2, comprises an amino acid substitution selected from the group consisting of A156G, A156T, and A156V.

3. The variant protease according to claim 1 or 2, further comprising one or more amino acid substitutions selected from the group consisting of S20N, R26K, Q28R, A39T, Q41R, I71V, Q80R, Q86R, P89L, P89S, S101N, A111S, P115S, S122R, R155Q, L144F, A150V, R155W, V158L, D168A, D168G, D168H, D168N, D168V, E176K, T178S, M179I, M179V, and M179T.

4. An isolated, variant, inhibitor-resistant, HCV NS3 protease comprising an amino acid sequence which is at least 90% identical to the amino acid sequence of SEQ ID NO:2, wherein said variant comprises an amino acid substitution at the position corresponding to position 156 of SEQ ID NO:2 selected from the group consisting of A156G, A156T, and A156V.

5. The variant protease according to claim 4, further comprising one or more amino acid substitutions selected from the group consisting of S20N, R26K, Q28R, A39T, Q41R, I71V, Q80R, Q86R, P89L, P89S, S101N, A111S, P115S, S122R, R155Q, L144F, A150V, R155W, V158L, D168A, D168G, D168H, D168N, D168V, E176K, T178S, M179I, M179V, and M179T.

6. A method for identifying inhibitor of HCV NS3 protease activity comprising:

incubating an inhibitor-resistant NS3 protease variant as defined in claim 1 in the presence or absence of a candidate inhibitor compound; and measuring the protease activity of said inhibitor-resistant NS3 protease in the presence and absence of said candidate inhibitor compound;

wherein a decrease in activity of said protease in the presence of a candidate inhibitor indicates that said compound inhibits said HCV NS3 protease.

* * * * *